(12) United States Patent
Hara et al.

(10) Patent No.: US 8,969,520 B2
(45) Date of Patent: Mar. 3, 2015

(54) REAGENT FOR ASSAYING ANTI-TREPONEMA PALLIDUM ANTIBODY

(75) Inventors: Yasuyuki Hara, Ryugasaki (JP); Tetsuya Ota, Ryugasaki (JP); Michiko Kawamoto, Ryugasaki (JP); Shinya Sato, Fukuyama (JP); Shigehisa Iwamoto, Fukuyama (JP); Tatsuro Shimaoka, Fukuyama (JP); Shigeo Sudo, Fukuyama (JP)

(73) Assignees: Sekisui Medical Co., Ltd., Tokyo (JP); Japan-Lamb Inc., Fukuyama-shi (JP)

(*) Notice: Subject to any disclaimer, the term of this patent is extended or adjusted under 35 U.S.C. 154(b) by 0 days.

(21) Appl. No.: 13/638,622

(22) PCT Filed: Mar. 31, 2011

(86) PCT No.: PCT/JP2011/058282
§ 371 (c)(1),
(2), (4) Date: Oct. 1, 2012

(87) PCT Pub. No.: WO2011/125872
PCT Pub. Date: Oct. 13, 2011

(65) Prior Publication Data
US 2013/0143229 A1 Jun. 6, 2013

(30) Foreign Application Priority Data
Mar. 31, 2010 (JP) ................. 2010-083822

(51) Int. Cl.
*C07K 14/20* (2006.01)
*G01N 33/571* (2006.01)
*G01N 33/545* (2006.01)
*A61K 39/02* (2006.01)
*G01N 33/68* (2006.01)

(52) U.S. Cl.
CPC .............. *C07K 14/20* (2013.01); *G01N 33/571* (2013.01); *G01N 33/6854* (2013.01); *G01N 33/545* (2013.01); *G01N 2333/20* (2013.01); *G01N 2469/20* (2013.01)
USPC .......................... 530/350; 435/7.1; 424/262.1

(58) Field of Classification Search
CPC ... C07K 14/20; G01N 33/571; G01N 2333/20
See application file for complete search history.

(56) References Cited

U.S. PATENT DOCUMENTS

| | | | |
|---|---|---|---|
| 4,868,118 A | 9/1989 | Norgard | |
| 5,350,842 A | 9/1994 | Norgard | |
| 5,578,456 A | 11/1996 | Fujimura et al. | |
| 5,681,934 A | 10/1997 | Norgard | |
| 6,479,248 B1 * | 11/2002 | Krell et al. | 435/7.22 |

FOREIGN PATENT DOCUMENTS

| | | |
|---|---|---|
| JP | 7 287017 | 10/1995 |
| JP | 9 257799 | 10/1997 |
| JP | 10 213585 | 8/1998 |
| JP | 11 287804 | 10/1999 |
| JP | 2001 264334 | 9/2001 |
| JP | 2003-337134 A | 11/2003 |
| WO | 88 02403 | 4/1988 |
| WO | WO 00/47613 A1 | 8/2000 |

OTHER PUBLICATIONS

Ebel et al 2000 Journal of Clinical Microbiology, vol. 38, No. 1, p. 215-219.*
Chain A, Tp47, The 47-Kilodalton Lipoprotein of Treponema Pallidum at http://www.ncbi.nlm.nih.gov/protein/1075_A accessed Jul. 30, 2014.
Chain B, Tp47, The 47-Kilodalton Lipoprotein of Treponema Pallidum at http://www.ncbi.nlm.nih.gov/protein/1075_B accessed Jul. 30, 2014.
Hand-Annotated Fig. 3 of WO00/47613, 2000.
English translation of WO00/47613, 2000.
Extended European Search Report issued Jun. 3, 2013 in Patent Application No. 11765772.6.
Guo Qing-shun et al., "Expression of Treponema pallidum 47 ku Fragments and Analysis of Its Epitope", Xiamen Daxue Xuebao (Ziran Kexue Ban)—Xiamen University Journal (Natural Science Edition), vol. 47, No. 6, XP009158846, Nov. 1, 2008, pp. 874-878 with English abstract.
Deka, R.K., et al., "Crystal Structure of the 47-kDA Lipoprotein in *Treponema pallidum* Reveals a Novel Penicillin-binding Protein," The Journal of Biologcal Chemistry, vol. 277, No. 44, pp. 41857-41864, (2002).
Weigel, L.M., et al., "Analysis of the N-Terminal Region of the 47-Kilodalton Integral Membrane Lipoprotein of *Treponema pallidum*," Infection and Immunity, vol. 60, No. 4, pp. 1568-1576, (1992).
Baughn, R.E., et al., "Molecular Mimicry Between an Immunodominant Amino Acid Motif on the 47-kDa Lipoprotein *Treponema pallidum* (Tpp47) and Multiple Repeats of Analogous Sequences in Fibronectin," Journal of Immunology, vol. 157, No. 2, pp. 720-731, (Jul. 15, 1996).
"MMDB Protein Structure Summary," NCBI (National Center for Biotechnology Information), MMDB ID: 21051, Total 2 Pages, (May 2011).
Weigel, L.M., et al., "The 47-kDa major lipoprotein immunogen of *Treponema pallidum* is a penicillin-binding protein with carboxypeptidase activity," Proceedings of the National Academy of Scienece, vol. 91, pp. 11611-11615, (Nov. 1994).
International Search Report Issued May 17, 2011 in PCT/JP11/58282 Filed Mar. 31, 2011.

* cited by examiner

Primary Examiner — Padma V Baskar
(74) Attorney, Agent, or Firm — Oblon, McClelland, Maier & Neustadt, L.L.P.

(57) ABSTRACT

To provide a reagent for assaying anti-*Treponema pallidum* antibody which reagent contains a polypeptide antigen and which reagent provides high assay sensitivity and high specificity, and to provide an assay method employing the assay reagent.
The reagent for assaying anti-*Treponema pallidum* antibody, for use in an assay of anti-*Treponema pallidum* antibody on the basis of antigen-antibody reaction is characterized in that the reagent contains, as an antigen, a recombinant polypeptide containing at least domain C and domain D of *Treponema pallidum* 47 kDa antigen but containing no domain A1 of the 47 kDa antigen.

14 Claims, 5 Drawing Sheets

SEQUENCE LISTING

<160> NUMBER OF SEQ ID NOS: 42

<210> SEQ ID NO 1
<211> LENGTH: 25
<212> TYPE: DNA
<213> ORGANISM: Artificial sequence
<220> FEATURE:
<223> OTHER INFORMATION: primer for Treponema gene

<400> SEQUENCE: 1
ggatcctgtg gctcgtctca tcacg                                    25

<210> SEQ ID NO 2
<211> LENGTH: 65
<212> TYPE: DNA
<213> ORGANISM: Artificial sequence
<220> FEATURE:
<223> OTHER INFORMATION: primer for Treponema gene

<400> SEQUENCE: 2
ccggcccagt aatccgcata gctcagcgtc gcatagccat aatgcgtttc gtgatgagac    60
gagcc                                                          65

<210> SEQ ID NO 3
<211> LENGTH: 75
<212> TYPE: DNA
<213> ORGANISM: Artificial sequence
<220> FEATURE:
<223> OTHER INFORMATION: primer for Treponema gene

<400> SEQUENCE: 3
ggattactgg gccggtgagc tggggcagag tcgcgacgtg ctgttggcgg gtaatgccga    60
agccgatcgc gcggg                                               75

<210> SEQ ID NO 4
<211> LENGTH: 75
<212> TYPE: DNA
<213> ORGANISM: Artificial sequence
<220> FEATURE:
<223> OTHER INFORMATION: primer for Treponema gene

<400> SEQUENCE: 4
aacgcgccat gcccatgggt tgcgcgggaa actgcatcga acatgcctgc gtcgagatca    60
cccgcgcgat cggct                                               75

<210> SEQ ID NO 5
<211> LENGTH: 75
<212> TYPE: DNA
<213> ORGANISM: Artificial sequence
<220> FEATURE:
<223> OTHER INFORMATION: primer for Treponema gene

<400> SEQUENCE: 5
tgggcatggc gcgttccgtc agcaatttca gtatgcggtt gaggtactgg gcgaaaaggt    60
cctgtcgaaa caaga                                               75

<210> SEQ ID NO 6
<211> LENGTH: 58
<212> TYPE: DNA
<213> ORGANISM: Artificial sequence
<220> FEATURE:
<223> OTHER INFORMATION: primer for Treponema gene

<400> SEQUENCE: 6
agtttcgtac tcccatttct tacgaccgcg gctatcttcg gtctcttgtt tcgacagg        58

<210> SEQ ID NO 7
<211> LENGTH: 33
<212> TYPE: DNA
<213> ORGANISM: Artificial sequence
<220> FEATURE:
<223> OTHER INFORMATION: primer for Treponema gene

<400> SEQUENCE: 7
tgggagtacg aaactgaccc aagcgttacc aaa                                   33

<210> SEQ ID NO 8
<211> LENGTH: 75
<212> TYPE: DNA
<213> ORGANISM: Artificial sequence
<220> FEATURE:
<223> OTHER INFORMATION: primer for Treponema gene

<400> SEQUENCE: 8
ttcaaactta atctcgccgt cttcgcccag atcctgaaat gacgcagagg cacgcaccat     60
tttggtaacg cttgg                                                      75

<210> SEQ ID NO 9
<211> LENGTH: 75
<212> TYPE: DNA
<213> ORGANISM: Artificial sequence
<220> FEATURE:
<223> OTHER INFORMATION: primer for Treponema gene

<400> SEQUENCE: 9
gagattaagt ttgaagcagt cgaaggtgca gtagccttag cggatcgtgc cagttccttc     60
atggttgaca gcgag                                                      75

<210> SEQ ID NO 10
<211> LENGTH: 75
<212> TYPE: DNA
<213> ORGANISM: Artificial sequence
<220> FEATURE:
<223> OTHER INFORMATION: primer for Treponema gene

<400> SEQUENCE: 10
aggaaccgca actgggacaa acttcatacc gtgaactttt acgttcgtaa ttttgtattc     60
ctcgctgtca accat                                                      75

<210> SEQ ID NO 11
<211> LENGTH: 75
<212> TYPE: DNA
<213> ORGANISM: Artificial sequence
<220> FEATURE:
<223> OTHER INFORMATION: primer for Treponema gene

<400> SEQUENCE: 11
ccagttgcgg ttcctcatga actgaaaggc attgcaaaag agaagtttca cttcgtggaa     60
gattcccgcg ttacg                                                      75

<210> SEQ ID NO 12
<211> LENGTH: 75
<212> TYPE: DNA
<213> ORGANISM: Artificial sequence
<220> FEATURE:
<223> OTHER INFORMATION: primer for Treponema gene

<400> SEQUENCE: 12
tactttacgt gcggaaaaac tatcttcggt gagcattgtt ttaaggccgt tggtattctc      60
cgtaacgcgg gaatc                                                       75

<210> SEQ ID NO 13
<211> LENGTH: 33
<212> TYPE: DNA
<213> ORGANISM: Artificial sequence
<220> FEATURE:
<223> OTHER INFORMATION: primer for Treponema gene

<400> SEQUENCE: 13
tccgcacgta aagtaagctc gatggaaagc ccg                                   33

<210> SEQ ID NO 14
<211> LENGTH: 75
<212> TYPE: DNA
<213> ORGANISM: Artificial sequence
<220> FEATURE:
<223> OTHER INFORMATION: primer for Treponema gene

<400> SEQUENCE: 14
tgcgtccgaa ccaaaacggc tatggtaacc ggtacccacc gtatctacca caaggtcgtg      60
cgggctttcc atcga                                                       75

<210> SEQ ID NO 15
<211> LENGTH: 75
<212> TYPE: DNA
<213> ORGANISM: Artificial sequence
<220> FEATURE:
<223> OTHER INFORMATION: primer for Treponema gene

<400> SEQUENCE: 15
tttggttcgg acgcagaagc ttctgtgatg ctgaaacgcg ctgatggctc cgaactgagc      60
catcgtgagt tcatc                                                       75

<210> SEQ ID NO 16
<211> LENGTH: 75
<212> TYPE: DNA
<213> ORGANISM: Artificial sequence
<220> FEATURE:
<223> OTHER INFORMATION: primer for Treponema gene

<400> SEQUENCE: 16
gtagctggcg tcatcaccat agtaatcata gcggaccgtg ttgaagttca tcacatagtc      60
gatgaactca cgatg                                                       75

<210> SEQ ID NO 17
<211> LENGTH: 75
<212> TYPE: DNA
<213> ORGANISM: Artificial sequence
<220> FEATURE:
<223> OTHER INFORMATION: primer for Treponema gene

<400> SEQUENCE: 17
gatgacgcca gctacaccaa tctgatggcg agttatggca ccaaacactc ggctgattcc      60
tggtggaaga caggt                                                       75

<210> SEQ ID NO 18
<211> LENGTH: 75
<212> TYPE: DNA
<213> ORGANISM: Artificial sequence

```
<220> FEATURE:
<223> OTHER INFORMATION: primer for Treponema gene

<400> SEQUENCE: 18
acctgagcct ttaaagcgat cgaacccata gttgataccg cacgaaatgc gcggcacacg    60
acctgtcttc cacca                                                    75

<210> SEQ ID NO 19
<211> LENGTH: 39
<212> TYPE: DNA
<213> ORGANISM: Artificial sequence
<220> FEATURE:
<223> OTHER INFORMATION: primer for Treponema gene

<400> SEQUENCE: 19
tttaaaggct caggtccggg ttattaccgt ctgactttg                           39

<210> SEQ ID NO 20
<211> LENGTH: 75
<212> TYPE: DNA
<213> ORGANISM: Artificial sequence
<220> FEATURE:
<223> OTHER INFORMATION: primer for Treponema gene

<400> SEQUENCE: 20
cccttcgtat ttcggcagga agcgcacatc agcaactacg tcacgatagc cgttggcaat    60
caaagtcaga cggta                                                    75

<210> SEQ ID NO 21
<211> LENGTH: 75
<212> TYPE: DNA
<213> ORGANISM: Artificial sequence
<220> FEATURE:
<223> OTHER INFORMATION: primer for Treponema gene

<400> SEQUENCE: 21
ccgaaatacg aagggaacat cgatattggc ttgaagggca aagtgctgac catcggggt    60 gcggacgccg aaacc                                                    75

<210> SEQ ID NO 22
<211> LENGTH: 75
<212> TYPE: DNA
<213> ORGANISM: Artificial sequence
<220> FEATURE:
<223> OTHER INFORMATION: primer for Treponema gene

<400> SEQUENCE: 22
ttgatcgctg acaagtttag gttggccatc ggcaaacacg tcaactgcag catccatcag    60
ggtttcggcg tccgc                                                    75

<210> SEQ ID NO 23
<211> LENGTH: 75
<212> TYPE: DNA
<213> ORGANISM: Artificial sequence
<220> FEATURE:
<223> OTHER INFORMATION: primer for Treponema gene

<400> SEQUENCE: 23
cttgtcagcg atcaagcggt gagcctgggg cagaatgtcc tctctgcgga tttcactccg    60
ggcaccgaat acacg                                                    75

<210> SEQ ID NO 24
```

```
<211> LENGTH: 75
<212> TYPE: DNA
<213> ORGANISM: Artificial sequence
<220> FEATURE:
<223> OTHER INFORMATION: primer for Treponema gene

<400> SEQUENCE: 24
ctcgagctac tgggccacta ctttcgcacg cacagaaccg aactctttga agcgcacttc      60
aaccgtgtat tcggt                                                      75

<210> SEQ ID NO 25
<211> LENGTH: 19
<212> TYPE: DNA
<213> ORGANISM: Artificial sequence
<220> FEATURE:
<223> OTHER INFORMATION: primer for Treponema gene

<400> SEQUENCE: 25
ggatcccgga ccctggaac                                                  19

<210> SEQ ID NO 26
<211> LENGTH: 21
<212> TYPE: DNA
<213> ORGANISM: Artificial sequence
<220> FEATURE:
<223> OTHER INFORMATION: primer for Treponema gene

<400> SEQUENCE: 26
ggtaatgccg aagccgatcg c                                               21

<210> SEQ ID NO 27
<211> LENGTH: 21
<212> TYPE: DNA
<213> ORGANISM: Artificial sequence
<220> FEATURE:
<223> OTHER INFORMATION: primer for Treponema gene

<400> SEQUENCE: 27
cttcataccg tgaacttta c                                                21

<210> SEQ ID NO 28
<211> LENGTH: 20
<212> TYPE: DNA
<213> ORGANISM: Artificial sequence
<220> FEATURE:
<223> OTHER INFORMATION: primer for Treponema gene

<400> SEQUENCE: 28
tttgtcccag ttgcggttcc                                                 20

<210> SEQ ID NO 29
<211> LENGTH: 21
<212> TYPE: DNA
<213> ORGANISM: Artificial sequence
<220> FEATURE:
<223> OTHER INFORMATION: primer for Treponema gene

<400> SEQUENCE: 29
ttccatcgag cttactttac g                                               21

<210> SEQ ID NO 30
<211> LENGTH: 17
<212> TYPE: DNA
<213> ORGANISM: Artificial sequence
<220> FEATURE:
<223> OTHER INFORMATION: primer for Treponema gene
```

<400> SEQUENCE: 30
agcccgcacg accttgt                                                    17

<210> SEQ ID NO 31
<211> LENGTH: 21
<212> TYPE: DNA
<213> ORGANISM: Artificial sequence
<220> FEATURE:
<223> OTHER INFORMATION: primer for Treponema gene

<400> SEQUENCE: 31
gtatttcggc aggaagcgca c                                               21

<210> SEQ ID NO 32
<211> LENGTH: 20
<212> TYPE: DNA
<213> ORGANISM: Artificial sequence
<220> FEATURE:
<223> OTHER INFORMATION: primer for Treponema gene

<400> SEQUENCE: 32
gaagggaaca tcgatattgg                                                 20

<210> SEQ ID NO 33
<211> LENGTH: 19
<212> TYPE: DNA
<213> ORGANISM: Artificial sequence
<220> FEATURE:
<223> OTHER INFORMATION: primer for Treponema gene

<400> SEQUENCE: 33
taactcgagc ggccgcatc                                                  19

<210> SEQ ID NO 34
<211> LENGTH: 639
<212> TYPE: DNA
<213> ORGANISM: Artificial sequence
<220> FEATURE:
<223> OTHER INFORMATION: CD domain of Treponema gene

<400> SEQUENCE: 34
ggatccagcc cgcacgacct tgtggtagat acggtgggta ccggttacca tagccgtttt      60
ggttcggacg cagaagcttc tgtgatgctg aaacgcgctg atggctccga actgagccat 120
cgtgagttca tcgactatgt gatgaacttc aacacggtcc gctatgatta ctatggtgat 180
gacgccagct acaccaatct gatggcgagt tatggcacca aacactcggc tgattcctgg 240
tggaagacag gtcgtgtgcc gcgcatttcg tgcggtatca actatgggtt cgatcgcttt 300
aaaggctcag gtccgggtta ttaccgtctg actttgattg ccaacggcta tcgtgacgta 360
gttgctgatg tgcgcttcct gccgaaatac gaagggaaca tcgatattgg cttgaagggc 420
aaagtgctga ccatcggggg tgcggacgcc gaaaccctga tggatgctgc agttgacgtg 480
tttgccgatg gccaacctaa acttgtcagc gatcaagcgg tgagcctggg gcagaatgtc 540
ctctctgcgg atttcactcc gggcaccgaa tacacggttg aagtgcgctt caaagagttc 600
ggttctgtgc gtgcgaaagt agtggcccag tagctcgag 639

<210> SEQ ID NO 35
<211> LENGTH: 792
<212> TYPE: DNA
<213> ORGANISM: Artificial sequence
<220> FEATURE:

<223> OTHER INFORMATION: A2CD domain of Treponema gene

<400> SEQUENCE: 35

```
ggatcctttg tcccagttgc ggttcctcat gaactgaaag gcattgcaaa agagaagttt     60
cacttcgtgg aagattcccg cgttacggag aataccaacg gccttaaaac aatgctcacc    120
gaagatagtt tttccgcacg taaagtaagc tcgatggaaa gcccgcacga ccttgtggta    180
gatacggtgg gtaccggtta ccatagccgt tttggttcgg acgcagaagc ttctgtgatg    240
ctgaaacgcg ctgatggctc cgaactgagc catcgtgagt tcatcgacta tgtgatgaac    300
ttcaacacgg tccgctatga ttactatggt gatgacgcca gctacaccaa tctgatggcg    360
agttatggca ccaaacactc ggctgattcc tggtggaaga caggtcgtgt gccgcgcatt    420
tcgtgcggta tcaactatgg gttcgatcgc tttaaaggct caggtccggg ttattaccgt    480
ctgactttga ttgccaacgg ctatcgtgac gtagttgctg atgtgcgctt cctgccgaaa    540
tacgaaggga acatcgatat tggcttgaag ggcaaagtgc tgaccatcgg gggtgcggac    600
gccgaaaccc tgatggatgc tgcagttgac gtgtttgccg atggccaacc taaacttgtc    660
agcgatcaag cggtgagcct ggggcagaat gtcctctctg cggatttcac tccgggcacc    720
gaatacacgg ttgaagtgcg cttcaaagag ttcggttctg tgcgtgcgaa agtagtggcc    780
cagtagctcg ag                                                        792
```

<210> SEQ ID NO 36
<211> LENGTH: 1158
<212> TYPE: DNA
<213> ORGANISM: Artificial sequence
<220> FEATURE:
<223> OTHER INFORMATION: BA2CD domain of Treponema gene

<400> SEQUENCE: 36

```
ggatccggta atgccgaagc cgatcgcgcg ggtgatctcg acgcaggcat gttcgatgca     60
gtttcccgcg caacccatgg gcatggcgcg ttccgtcagc aatttcagta tgcggttgag    120
gtactgggcg aaaaggtcct gtcgaaacaa gagaccgaag atagccgcgg tcgtaagaaa    180
tgggagtacg aaactgaccc aagcgttacc aaaatggtgc gtgcctctgc gtcatttcag    240
gatctgggcg aagacggcga gattaagttt gaagcagtcg aaggtgcagt agccttagcg    300
gatcgtgcca gttccttcat ggttgacagc gaggaataca aaattacgaa cgtaaaagtt    360
cacggtatga agtttgtccc agttgcggtt cctcatgaac tgaaaggcat tgcaaaagag    420
aagtttcact tcgtggaaga ttcccgcgtt acggagaata ccaacggcct taaaacaatg    480
ctcaccgaag atagtttttc cgcacgtaaa gtaagctcga tggaaagccc gcacgacctt    540
gtggtagata cggtgggtac cggttaccat agccgttttg gttcggacgc agaagcttct    600
gtgatgctga aacgcgctga tggctccgaa ctgagccatc gtgagttcat cgactatgtg    660
atgaacttca acacggtccg ctatgattac tatggtgatg acgccagcta caccaatctg    720
atggcgagtt atggcaccaa acactcggct gattcctggt ggaagacagg tcgtgtgccg    780
cgcatttcgt gcggtatcaa ctatgggttc gatcgcttta aaggctcagg tccgggttat    840
taccgtctga ctttgattgc caacggctat cgtgacgtag ttgctgatgt gcgcttcctg    900
ccgaaatacg aagggaacat cgatattggc ttgaagggca aagtgctgac catcgggggt    960
gcggacgccg aaaccctgat ggatgctgca gttgacgtgt ttgccgatgg ccaacctaaa   1020
cttgtcagcg atcaagcggt gagcctgggg cagaatgtcc tctctgcgga tttcactccg   1080
ggcaccgaat acacggttga agtgcgcttc aaagagttcg gttctgtgcg tgcgaaagta   1140
```

<210> SEQ ID NO 37
<211> LENGTH: 1020
<212> TYPE: DNA
<213> ORGANISM: Artificial sequence
<220> FEATURE:
<223> OTHER INFORMATION: A1BA2C domain of Treponema gene

<400> SEQUENCE: 37

```
ggatcctgtg gctcgtctca tcacgaaacg cattatggct atgcgacgct gagctatgcg      60
gattactggg ccggtgagct ggggcagagt cgcgacgtgc tgttggcggg taatgccgaa     120
gccgatcgcg cgggtgatct cgacgcaggc atgttcgatg cagtttcccg cgcaacccat     180
gggcatggcg cgttccgtca gcaatttcag tatgcggttg aggtactggg cgaaaaggtc     240
ctgtcgaaac aagagaccga agatagccgc ggtcgtaaga aatgggagta cgaaactgac     300
ccaagcgtta ccaaaatggt gcgtgcctct gcgtcatttc aggatctggg cgaagacggc     360
gagattaagt ttgaagcagt cgaaggtgca gtagccttag cggatcgtgc cagttccttc     420
atggttgaca gcgaggaata caaaattacg aacgtaaaag ttcacggtat gaagtttgtc     480
ccagttgcgg ttcctcatga actgaaaggc attgcaaaag agaagtttca cttcgtggaa     540
gattcccgcg ttacggagaa taccaacggc cttaaaacaa tgctcaccga agatagtttt     600
tccgcacgta aagtaagctc gatggaaagc ccgcacgacc ttgtggtaga tacggtgggt     660
accggttacc atagccgttt tggttcggac gcagaagctt ctgtgatgct gaaacgcgct     720
gatggctccg aactgagcca tcgtgagttc atcgactatg tgatgaactt caacacggtc     780
cgctatgatt actatggtga tgacgccagc tacaccaatc tgatggcgag ttatggcacc     840
aaacactcgg ctgattcctg gtggaagaca ggtcgtgtgc cgcgcatttc gtgcggtatc     900
aactatgggt tcgatcgctt taaaggctca ggtccgggtt attaccgtct gactttgatt     960
gccaacggct atcgtgacgt agttgctgat gtgcgcttcc tgccgaaata ctaactcgag    1020
```

<210> SEQ ID NO 38
<211> LENGTH: 636
<212> TYPE: DNA
<213> ORGANISM: Artificial sequence
<220> FEATURE:
<223> OTHER INFORMATION: A1BA2 domain of Treponema gene

<400> SEQUENCE: 38

```
ggatcctgtg gctcgtctca tcacgaaacg cattatggct atgcgacgct gagctatgcg      60
gattactggg ccggtgagct ggggcagagt cgcgacgtgc tgttggcggg taatgccgaa     120
gccgatcgcg cgggtgatct cgacgcaggc atgttcgatg cagtttcccg cgcaacccat     180
gggcatggcg cgttccgtca gcaatttcag tatgcggttg aggtactggg cgaaaaggtc     240
ctgtcgaaac aagagaccga agatagccgc ggtcgtaaga aatgggagta cgaaactgac     300
ccaagcgtta ccaaaatggt gcgtgcctct gcgtcatttc aggatctggg cgaagacggc     360
gagattaagt ttgaagcagt cgaaggtgca gtagccttag cggatcgtgc cagttccttc     420
atggttgaca gcgaggaata caaaattacg aacgtaaaag ttcacggtat gaagtttgtc     480
ccagttgcgg ttcctcatga actgaaaggc attgcaaaag agaagtttca cttcgtggaa     540
gattcccgcg ttacggagaa taccaacggc cttaaaacaa tgctcaccga agatagtttt     600
tccgcacgta aagtaagctc gatggaataa ctcgag                              636
```

<210> SEQ ID NO 39
<211> LENGTH: 381
<212> TYPE: DNA
<213> ORGANISM: Artificial sequence
<220> FEATURE:
<223> OTHER INFORMATION: B domain of Treponema gene

<400> SEQUENCE: 39
ggatccggta atgccgaagc cgatcgcgcg ggtgatctcg acgcaggcat gttcgatgca 60
gtttcccgcg caacccatgg gcatggcgcg ttccgtcagc aatttcagta tgcggttgag 120
gtactgggcg aaaaggtcct gtcgaaacaa gagaccgaag atagccgcgg tcgtaagaaa 180
tgggagtacg aaactgaccc aagcgttacc aaaatggtgc gtgcctctgc gtcatttcag 240
gatctgggcg aagacggcga gattaagttt gaagcagtcg aaggtgcagt agccttagcg 300
gatcgtgcca gttccttcat ggttgacagc gaggaataca aaattacgaa cgtaaaagtt 360
cacggtatga agtaactcga g 381

<210> SEQ ID NO 40
<211> LENGTH: 399
<212> TYPE: DNA
<213> ORGANISM: Artificial sequence
<220> FEATURE:
<223> OTHER INFORMATION: C domain of Treponema gene

<400> SEQUENCE: 40
ggatccagcc cgcacgacct tgtggtagat acggtgggta ccggttacca tagccgtttt 60
ggttcggacg cagaagcttc tgtgatgctg aaacgcgctg atggctccga actgagccat 120
cgtgagttca tcgactatgt gatgaacttc aacacggtcc gctatgatta ctatggtgat 180
gacgccagct acaccaatct gatggcgagt tatggcacca aacactcggc tgattcctgg 240
tggaagacag gtcgtgtgcc gcgcatttcg tgcggtatca actatgggtt cgatcgcttt 300
aaaggctcag gtccgggtta ttaccgtctg actttgattg ccaacggcta tcgtgacgta 360
gttgctgatg tgcgcttcct gccgaaatac taactcgag 399

<210> SEQ ID NO 41
<211> LENGTH: 255
<212> TYPE: DNA
<213> ORGANISM: Artificial sequence
<220> FEATURE:
<223> OTHER INFORMATION: D domain of Treponema gene

<400> SEQUENCE: 41
ggatccgaag ggaacatcga tattggcttg aagggcaaag tgctgaccat cgggggtgcg 60
gacgccgaaa ccctgatgga tgctgcagtt gacgtgtttg ccgatggcca acctaaactt 120
gtcagcgatc aagcggtgag cctggggcag aatgtcctct ctgcggattt cactccgggc 180
accgaataca cggttgaagt gcgcttcaaa gagttcggtt ctgtgcgtgc gaaagtagtg 240
gcccagtagc tcgag 255

<210> SEQ ID NO 42
<211> LENGTH: 507
<212> TYPE: DNA
<213> ORGANISM: Artificial sequence
<220> FEATURE:
<223> OTHER INFORMATION: DNA fragment of Cry protein gene

<400> SEQUENCE: 42
ggatccatca tcaacacctt ctacgcaaac ccgatcaaga acaccctgca atcggaactg 60

-continued

```
accgactacg acatcgacca agcggcaaat ctggtggaat gtattagcga agagttgtac    120
ccgaaagaaa agatgctgtt gttggacgaa gtgaagaacg caaagcaact gagccaatcg    180
cgtaacgtgc tgcaaaacgg cgacttcgaa tcggctacgc tgggttggac cacgagcgac    240
aatatcacca ttcaagaaga cgatccgatt ttcaaaggcc attacctgca catgtccggc    300
gcgcgtgaca tcgatggtac catcttcccg acctacatct tccaaaagat cgatgaatcg    360
aaattgaagc cgtacacccg ttacctggtg cgtggtttcg tgggtagcag caaggacgtc    420
gaactggtgg tctcgcgcta cggcgaagaa atcgatgcaa tcatgaatgt gccggcactg    480
gaagtgctgt tccagggtcc gggatcc                                        507
```

REAGENT FOR ASSAYING ANTI-TREPONEMA PALLIDUM ANTIBODY

FIELD OF THE INVENTION

The present invention relates to a reagent for assaying anti-*Treponema pallidum* antibody providing high assay sensitivity and high specificity, and to an assay method employing the assay reagent.

BACKGROUND OF THE INVENTION

Syphilis is a disease triggered through infection with *Treponema pallidum*. By virtue of development of an effective therapeutic agent (e.g., penicillin), the incidence of syphilis has decreased since the 1940s. However, the incidence has tended to increase in recent years. One characteristic feature of recent years' new-type syphilis patients resides in that many syphilis patients have a complication of HIV infection. Conceivable reasons for such high complication rate are that syphilis and HIV are sexually transmitted diseases, and that syphilis increases the risk of HIV infection. Under such circumstances, early detection and treatment of syphilis patients are required for preventing prevalence of infection with syphilis and HIV.

Whether or not a subject has contracted syphilis is determined through immunologically detecting an anti-*Treponema pallidum* antibody in blood. Meanwhile, there are a large number of surface antigens on the surface of a cell of *Treponema pallidum*, and syphilis is detected through an immunological assay based on antigen-antibody reaction between the surface antigens and an anti-*Treponema pallidum* antibody present in a sample. Known surface antigens present on the surface of a cell of *Treponema pallidum* mainly include antigens having molecular weights of 47 kDa, 42 kDa, 37 kDa, 17 kDa, and 15 kDa.

Currently, the surface antigen of *Treponema pallidum* cells employed in diagnosis of syphilis is produced through culturing *Treponema pallidum* cells in the testicles of rabbits, solubilizing and extracting the cells with a surfactant or the like, and purifying the target cells through various methods for removing impurities. Since the thus-prepared antigen derived from *Treponema pallidum* has high specificity to an anti-*Treponema pallidum* antibody, the antigen enables early detection of syphilis in patients. However, when the antigen is produced through the aforementioned antigen production method employing rabbits, a certain limitation is imposed on the yield of antigen, due to use of the testicles of rabbits as hosts. In addition, the state of growth of *Treponema pallidum* varies among the host rabbits, and difficulty is countered in consistent production of *Treponema pallidum* in a large amount. Notably, at present, direct artificial culturing of *Treponema pallidum* has never been attained.

In recent years, there has been proposed a method for producing a surface antigen of *Treponema pallidum* cells through a recombination technique. The gene encoding syphilis 47 kDa antigen has already been cloned, and the amino acid sequence formed of 415 amino acids has been determined (see, for example, Non-Patent Documents 1 and 3). The crystal structure and biological roles of the syphilis 47 kDa antigen have already been reported. It has been elucidated that the antigen is known to have four structural domains A, B, C, and D (see, for example, Non-Patent Documents 2 and 3).

Non-Patent Document 3 discloses that domain A is formed of amino acid 1 to amino acid 34 (A1 domain) and amino acid 157 to amino acid 207 (A2 domain), that domain B is formed of amino acid 35 to amino acid 156, that domain C is formed of amino acid 208 to amino acid 335, and that domain D is formed of amino acid 336 to amino acid 415, the positions of the amino acids being counted from the N-terminus (see Non-Patent Document 3, FIG. 1).

The aforementioned 47 kDa antigen has been reported to have an antibody recognition site formed of an amino acid sequence having antigen activity (see, for example, Non-Patent Document 4).

There has been disclosed an anti-*Treponema pallidum* antibody assay method employing the aforementioned antigen. In the disclosed method, syphilis 47 kDa antigen is produced through a recombination technique, and an anti-*Treponema pallidum* antibody is immunologically determined by use of the produced antigen (see Patent Document 1). A similar assay method employing a fusion protein between the N-terminus of 15 kDa or 17 kDa antigen and glutathione-S-transferase is also disclosed (see Patent Document 2).

In addition to antigen production through a recombination technique, there is also disclosed another anti-*Treponema pallidum* antibody assay method including synthesizing a peptide having 47 kDa antigen activity and employing the peptide as an antigen (see Patent Document 3).

PRIOR ART DOCUMENTS

Patent Documents

Patent Document 1: WO1988/02403
Patent Document 2: JP-A-H07-287017
Patent Document 3: JP-A-2001-264334

Non-Patent Documents

Non-Patent Document 1: Infection and Immunity, Vol. 60(4), p. 1568-1576 (1992)
Non-Patent Document 2: The Journal of Biological Chemistry, Vol. 277(44), p. 41857-41864 (2002)
Non-Patent Document 3: NCBI (National Center for Biotechnology Information), MMDB ID: 21051
Non-Patent Document 4: Journal of immunology, Vol. 157, p. 720-731 (1996)

SUMMARY OF THE INVENTION

Problems to be Solved by the Invention

Through use of such a *Treponema pallidum* recombinant antigen or a *Treponema pallidum* synthetic peptide antigen which is produced through the aforementioned methods, the anti-*Treponema pallidum* antibody can be assayed to some extent. However, anti-*Treponema pallidum* recombinant antigens produced through a genetic engineering technique provide problematically low assay sensitivity and assay specificity. The same problems arise in synthetic peptide antigens, and several peptides must be used in combination in order to assay anti-*Treponema pallidum* antibody with high accuracy. The assay employing synthetic peptides involves also cumbersome operations.

Although the reasons why the above problems occur have not been elucidated, a conceivable reason is as follows. Specifically, an anti-*Treponema pallidum* recombinant antigen produced through a genetic engineering technique is thought to have a structure, a lipid modification feature, etc., which are different from those of a naturally occurring antigen derived from *Treponema pallidum*. Generally, protein receives various modifications after completion of translation, typically modifications with saccharide, lipid, or the like. When a protein has undergone such a modification, the structure thereof varies. In contrast, a protein expressed from *E. coli*—generally employed in genetic engineering—does not receive modification after completion of translation. The protein structure is an important factor for exerting its antigenicity. Since a recombinant protein produced through a genetic engineering technique does not receive modification after translation, variation in protein structure is more considerable as compared with naturally occurring antigen, which conceivably affects the sensitivity and specificity.

In view of the foregoing, an object of the present invention is to provide a reagent for assaying anti-*Treponema pallidum* antibody, which reagent comprises a polypeptide antigen and which provides high assay sensitivity and high specificity. Another object of the invention is to provide an assay method employing the assay reagent.

Means for Solving the Problems

The present inventors have selected a molecular weight 47 kDa antigen, which is an antigen present on the surfaces of *Treponema pallidum* cells, and have produced the 47 kDa antigen and a partial polypeptide thereof through a genetic engineering technique. The inventors have conducted studies on the sensitivity and specificity of an anti-*Treponema pallidum* antibody reagent employing the genetic product. As a result, the inventors have found that a recombinant polypeptide formed of domain C or a recombinant polypeptide formed of domain D, as a single component, exhibits substantially no reactivity; that a recombinant polypeptide formed of domain C and domain D, a recombinant polypeptide formed of domain A2, domain C, and domain D, and a recombinant polypeptide formed of domain B, domain A2, domain C, and domain D exhibit remarkably enhanced sensitivity as compared with the recombinant 47 kDa antigen; and the sensitivity is comparable to that provided by a naturally occurring antigen. The present invention has been accomplished on the basis of these findings.

Accordingly, the present invention provides the following.
(1) A reagent for assaying anti-*Treponema pallidum* antibody, for use in an assay of anti-*Treponema pallidum* antibody on the basis of antigen-antibody reaction, characterized in that the reagent comprises, as an antigen, a recombinant polypeptide containing at least domain C and domain D of *Treponema pallidum* 47 kDa antigen but containing no domain A1 of the 47 kDa antigen.
(2) The anti-*Treponema pallidum* antibody assay reagent as described in (1) above, wherein the antigen is a recombinant polypeptide formed of domain C and domain D; domain A2, domain C, and domain D; or domain B, domain A2, domain C, and domain D, of *Treponema pallidum* 47 kDa antigen.
(3) The anti-*Treponema pallidum* antibody assay reagent as described in (1) above, wherein the antigen is supported on an insoluble carrier.
(4) The anti-*Treponema pallidum* antibody assay reagent as described in (2) above, wherein the antigen is supported on an insoluble carrier.
(5) The anti-*Treponema pallidum* antibody assay reagent as described in (3) above, wherein the insoluble carrier is a polymer latex.
(6) The anti-*Treponema pallidum* antibody assay reagent as described in (4) above, wherein the insoluble carrier is a polymer latex.
(7) A method for assaying anti-*Treponema pallidum* antibody, characterized in that the method employs an anti-*Treponema pallidum* antibody assay reagent as recited in (1) above.
(8) A method for assaying anti-*Treponema pallidum* antibody, characterized in that the method employs an anti-*Treponema pallidum* antibody assay reagent as recited in (2) above.
(9) A method for assaying anti-*Treponema pallidum* antibody, characterized in that the method employs an anti-*Treponema pallidum* antibody assay reagent as recited in (3) above.
(10) A method for assaying anti-*Treponema pallidum* antibody, characterized in that the method employs an anti-*Treponema pallidum* antibody assay reagent as recited in (4) above.
(11) A method for assaying anti-*Treponema pallidum* antibody, characterized in that the method employs an anti-*Treponema pallidum* antibody assay reagent as recited in (5) above.
(12) A method for assaying anti-*Treponema pallidum* antibody, characterized in that the method employs an anti-*Treponema pallidum* antibody assay reagent as recited in (6) above.

Effects of the Invention

The present invention employs a *Treponema pallidum* antigen recombinant polypeptide, which can consistently provide an antigen of uniform quality on a large scale and which realizes high-sensitivity and high-specificity assay of anti-*Treponema pallidum* antibody, whereby more accurate diagnosis of syphilis can be performed.

DETAILED DESCRIPTION OF THE INVENTION

Figure 1:
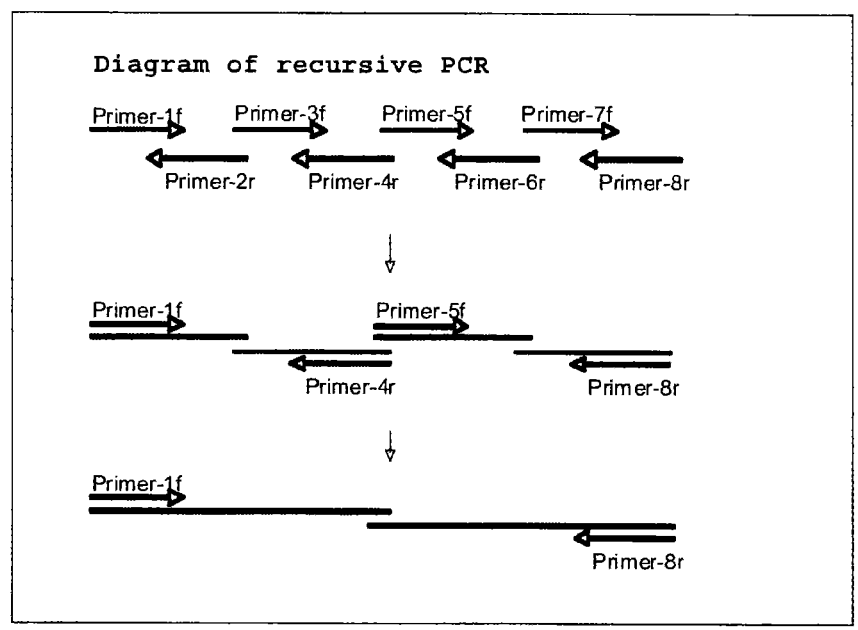
FIG. 1 A diagram of recursive PCR.
Figure 2:
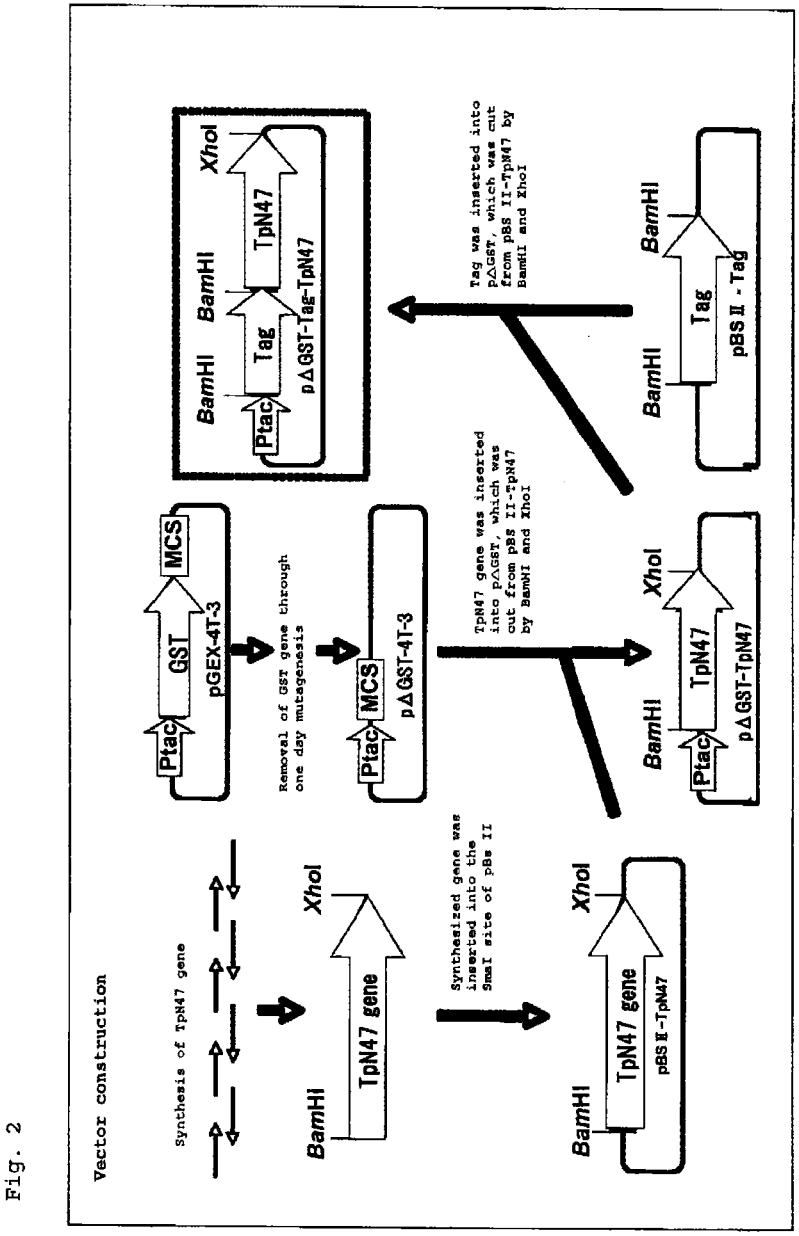
FIG. 2 A diagram of expression vector construction.

A characteristic feature of the anti-*Treponema pallidum* antibody assay reagent of the present invention based on antigen-antibody reaction resides in that the reagent comprises, as an antigen, a recombinant polypeptide containing at least domain C and domain D of *Treponema pallidum* 47 kDa antigen but containing no domain A1 of the 47 kDa antigen.

Specific examples of the recombinant polypeptide antigen employed in the present invention include a recombinant polypeptide formed of domain C and domain D; a recombinant polypeptide formed of domain A2, domain C, and domain D; and a recombinant polypeptide formed of domain B, domain A2, domain C, and domain D, these domains being parts of a molecular weight 47 kDa antigen, which is an antigen present on the surfaces of *Treponema pallidum* cells. Preferably, the recombinant polypeptide antigen is a recombinant polypeptide formed of domain C and domain D, or a recombinant polypeptide formed of domain A2, domain C, and domain D, since such a recombinant polypeptide has low molecular weight and has excellent correlation with a reagent produced by use of an antigen derived from *Treponema pal-*

*lidum* (Mediace (Registered trademark) TPLA, product of Sekisui Medical Co., Ltd.). More preferably, the recombinant polypeptide antigen is a recombinant polypeptide formed of domain C and domain D.

The polypeptide includes polypeptides having an amino acid sequence homology of 900 or higher, preferably 950 or higher, more preferably 98% or higher.

No particular limitation is imposed on the method for producing a DNA fragment encoding a polypeptide which is a part of the aforementioned 47 kDa antigen. Examples of the method include method i) including producing a full-length 47 kDa antigen gene through genetic cloning of syphilis bacterial cells or gene synthesis, removing a DNA fragment encoding an unnecessary polypeptide fragment by use of appropriate restriction enzymes or the like, and inserting the thus-obtained fragment into an expression vector; method ii) including producing a cDNA bank of syphilis bacterial cells, amplifying a DNA fragment encoding a relevant polypeptide through, for example, PCR by use of appropriate DNA primers, and inserting the DNA fragment into an expression vector; and method iii) including synthesizing a DNA fragment encoding a relevant polypeptide through direct synthesis or PCR or the like, and inserting the DNA fragment into an expression vector.

No particular limitation is imposed on the expression vector, and examples include plasmids, cosmids, phages, and viruses.

No particular limitation is imposed on the host in which the polypeptide encoded by the DNA sequence which is inserted into an expression vector is produced, and cultured cells, microorganisms such as *E. coli*, silkworms, etc. may be employed. Typically, the host is *E. coli*, or cultured cells.

In order to efficiently express the aforementioned polypeptides, or to facilitate purification of expression products, the target polypeptide may be expressed as a fusion protein with another protein (hereinafter referred to as "tag protein"). No particular limitation is imposed on the tag protein, and examples include β-galactosidase, glutathione-S-transferase, 6×histidine, and Cryprotein (disclosed in WO2010/013789), which is an insecticidal protein originating from *Bacillus thuringiensis*. In the case where a fusion protein is expressed, the tag protein is not necessarily removed in the purification step, and the as-purified fusion protein may be employed.

No particular limitation is imposed on the immunoassay reagent of the present invention. It can be used in methods for example immune agglutination, enzyme immunoassay (EIA), fluorescent immunoassay (FIA), and immunochromatography, . . . . A preferred method is immune agglutination employing the aforementioned antigen supported on an insoluble carrier.

No particular limitation is imposed on the insoluble carrier, and examples include organic polymer powder, microorganisms, blood cells, and cell membrane fragments. Of these, organic polymer powder is preferred. Examples of the organic polymer powder include natural polymer powder and synthetic polymer powder. Examples of the natural polymer powder include insoluble agarose, cellulose, and insoluble dextran, and examples of the synthetic polymer powder include polystyrene, styrene-sulfonic acid (salt) copolymer, styrene-methacrylic acid copolymer, acrylonitrile-butadiene-styrene copolymer, vinyl chloride-acrylate ester copolymer, and vinyl acetate-acrylate ester copolymer.

The surface of the aforementioned insoluble carrier may be modified with sulfonic acid groups, carboxyl groups, or amino groups.

The insoluble carrier is particularly preferably in the form of latex particles in which synthetic polymer powder is uniformly dispersed. Alternatively, there may be used plastic micro-titer plates; biological particles such as animal-derived erythrocytes and bacterial cells; and non-biological particles such as bentonite, collodion, cholesterol crystals, silica, kaolin, and carbon powder.

No particular limitation is imposed on the mean particle size of the latex particles, but it is preferably 0.05 μm to 1.5 μm as determined by means of an electron microscope. When the particle size of the latex particles is smaller than 0.05 μm, a change in optical density attributed to agglutination is small, thereby failing to obtain high sensitivity enabling measurement, whereas when the particle size of the latex particles is in excess of 1.5 μm change in optical density attributed to agglutination of latex particles exceeds a measurable range, thereby narrowing the measurable range. Thus, the lower limit of the particle size of the latex particles is preferably 0.1 μm, and the upper limit is more preferably 0.8 μm.

No particular limitation is imposed on the method of immobilizing the *Treponema pallidum* recombinant antigen onto the insoluble carrier, and a conventionally known physical or chemical supporting method may be employed. In one physical adsorption method, a recombinant antigen and an insoluble carrier are mixed under specific conditions, to thereby deposit the antigen onto the carrier. After the immobilization step, the insoluble carrier may be coated with an immunological inert substance such as albumin, casein, or a surfactant. In this case, albumin is preferably used.

No particular limitation is imposed on the origin of albumin, and albumin present in animal blood may be used. Examples of the animal include bovine, horse, rabbit, and goat. Human blood albumin may also be used. No particular limitation is imposed on the albumin level during the coating step, and the albumin level is preferably 0.01 wt. % to 10 wt. %. When the albumin level is lower than 0.01 wt. %, non-specific agglutination occurs due to insufficient coverage of the insoluble carrier surface, whereas when the albumin level is in excess of 10 wt. %, calibration curve sensitivity drops. Thus, the albumin level is preferably 0.1 to 5 wt. %.

In one method of coating the insoluble carrier with inert substance, a recombinant antigen is caused to be supported on an insoluble carrier, and the carrier is mixed with an inert substance under specific conditions. No particular limitation is imposed on the pH at reaction, and the pH is preferably 2 to 12. When the pH is lower than 2 or higher than 12, a problem such as denaturation of recombinant antigen occurs. Thus, the pH is more preferably 4 to 10. No particular limitation is imposed on the temperature at reaction, and the temperature is preferably 2° C. to 50° C. When the temperature is lower than 2° C., reaction fails to sufficiently proceed, or the reaction system is frozen, thereby failing to recover antigens having required sensitivity, whereas when the temperature is higher than 50° C., a problem such as denaturation of recombinant antigen occurs. Thus, the temperature is more preferably 2 to 10° C.

No particular limitation is imposed on the form of the thus-produced recombinant antigen-on-insoluble carrier. One embodiment is a suspension thereof in a buffer containing an immunologically inert substance. No particular limitation is imposed on the immunologically inert substance, and examples of suitably used inert substances include albumin, casein, surfactants (synthetic polymer compounds), synthetic phospholipids, polyvinylpyrrolidone, and polyethylene glycol. Of these, albumin and synthetic phospholipids are preferred.

No particular limitation is imposed on the solvent used in the aforementioned supporting-on-insoluble carrier step, inert-substance-coating step, and antigen-on-carrier suspending step. Examples of the solvent include phosphate buffer, Tris-HCl buffer, glycine buffer, and Good's buffer.

To the thus-produced suspension containing antigen-deposited latex particles, a sample is added and reacted with the antigen for a predetermined period of time. After the completion of the reaction, the degree of agglutination occurring by the antigen-antibody reaction between the recombinant antigen supported on the latex particles and the anti-*Treponema pallidum* antibody present in the sample is optically measured or visually confirmed, whereby the anti-*Treponema pallidum* antibody level of the sample can be determined.

No particular limitation is imposed on the method of optically measuring the agglutination degree, and a known technique is employed. Examples of the technique include turbidimetry in which formation of agglutination is measured as an increase in turbidity; a method in which formation of agglutination is measured as a change in particle size distribution or mean particle size; and integrating-sphere optical turbidimetry in which a change in forward-scattered light attributed to formation of agglutination (relative to transmitted light intensity) is measured by means of an integrating sphere. These methods may be employed in combination.

In the aforementioned measurement techniques, at least two measurements are obtained at different points in time, and the degree of agglutination is obtained on the basis of the rate of increase in the measurements between the time points (rate assay). Alternatively, the measurement is performed at a certain point in time (typically, a conceivable end point of reaction), and the degree of agglutination is obtained on the basis of the measurement (end point assay). From the viewpoints of simplicity and speed of the measurement, the rate assay based on turbidimetry is preferably performed.

The measurement is preferably performed at a light wavelength of 250 to 1,000 nm, more preferably 540 to 800 nm.

Examples of the apparatus employed in the above optical measurement include optical apparatuses which can detect scattered light intensity, transmitted light intensity, absorbance, or the like, and any of the generally employed biochemical automated analyzers may be employed.

In a typical mode of visually observing the degree of agglutination, a sample and a latex particle suspension are mixed together on a test plate, and the liquid mixture is shaken. Then, the presence of agglutination is determined. In addition to visual observation, the degree of agglutination may be imaged by means of a video camera or the like, followed by image analysis.

No particular limitation is imposed on the sample, so long as the sample may contain an anti-*Treponema* antibody. Examples of the sample include blood samples, plasma samples, and serum samples of humans and animals.

No particular limitation is imposed on the reaction mixture serving as the reaction system of the aforementioned antigen-antibody reaction, so long as the reaction mixture is an aqueous solution which ensures physiological conditions under which antigen-antibody reaction can occur. Examples of the aqueous solution include phosphate buffer, citrate buffer, glycine buffer, Tris buffer, and Good's buffer. The reaction mixture preferably has a pH of 4 to 10, more preferably 6 to 8.

If required, the reaction mixture may further contain a salt concentration-adjusting agent such as a stabilizer (e.g., bovine serum albumin or sucrose), an antiseptic such as sodium azide, or sodium chloride.

No particular limitation is imposed on the reaction temperature, so long as the aforementioned immunoreaction can occur. The reaction is preferably performed at a constant temperature of 10 to 50° C., more preferably 30 to 40° C. The reaction time may be appropriately predetermined.

EXAMPLES

The present invention will next be described in detail by way of Comparative Examples and Examples, which should not be construed as limiting the invention thereto.

(Primers for Preparing TpN47 Gene)

The premiers used for preparing a TpN47 gene (synthesized by a DNA synthesizer) are shown in Table 1. In the nucleotide sequences shown in Table 1, the underlined parts represent restriction enzyme sites required for sub-cloning to a vector.

TABLE 1

Primers for producing TpN47 gene

| name | sequence (5'→3') | length |
|---|---|---|
| TpN47_1f | <u>GGATCC</u>TGTGGCTCGTCTCATCACG (SEQ ID NO: 1) | 25 |
| TpN47_2r | CCGGCCCAGTAATCCGCATAGCTCAGCGTCGCATAGCCATAATGCGTT TCGTGATGAGACGAGCC (SEQ ID NO: 2) | 65 |
| TpN47_3f | GGATTACTGGGCCGGTGAGCTGGGGCAGAGTCGCGACGTGCTGTTGG CGGGTAATGCCGAAGCCGATCGCGCGGG (SEQ ID NO: 3) | 75 |
| TpN47_4r | AACGCGCCATGCCCATGGGTTGCGCGGGAAACTGCATCGAACATGCCT GCGTCGAGATCACCCGCGCGATCGGCT (SEQ ID NO: 4) | 75 |
| TpN47_5f | TGGGCATGGCGCGTTCCGTCAGCAATTTCAGTATGCGGTTGAGGTACT GGGCGAAAAGGTCCTGTCGAAACAAGA (SEQ ID NO: 5) | 75 |
| TpN47_6r | AGTTTCGTACTCCCATTTCTTACGACCGCGGCTATCTTCGGTCTCTTGT TTCGACAGG (SEQ ID NO: 6) | 58 |
| TpN47_7f | TGGGAGTACGAAACTGACCCAAGCGTTACCAAA (SEQ ID NO: 7) | 33 |
| TpN47_8r | TTCAAACTTAATCTCGCCGTCTTCGCCCAGATCCTGAAATGACGCAGA GGCACGCACCATTTTGGTAACGCTTGG (SEQ ID NO: 8) | 75 |
| TpN47_9f | GAGATTAAGTTTGAAGCAGTCGAAGGTGCAGTAGCCTTAGCGGATCGT GCCAGTTCCTTCATGGTTGACAGCGAG (SEQ ID NO: 9) | 75 |

TABLE 1-continued

Primers for producing TpN47 gene

| name | sequence (5'→3') | length |
|---|---|---|
| TpN47_10r | AGGAACCGCAACTGGGACAAACTTCATACCGTGAACTTTTACGTTCGT AATTTTGTATTCCTCGCTGTCAACCAT (SEQ ID NO: 10) | 75 |
| TpN47_11f | CCAGTTGCGGTTCCTCATGAACTGAAAGGCATTGCAAAAGAGAAGTTT CACTTCGTGGAAGATTCCCGCGTTACG (SEQ ID NO: 11) | 75 |
| TpN47_12r | TACTTTACGTGCGGAAAAACTATCTTCGGTGAGCATTGTTTTAAGGCCG TTGGTATTCTCCGTAACGCGGGAATC (SEQ ID NO: 12) | 75 |
| TpN47_13f | TCCGCACGTAAAGTAAGCTCGATGGAAAGCCCG (SEQ ID NO: 13) | 33 |
| TpN47_14r | TGCGTCCGAACCAAAACGGCTATGGTAACCGGTACCCACCGTATCTAC CACAAGGTCGTGCGGGCTTTCCATCGA (SEQ ID NO: 14) | 75 |
| TpN47_15f | TTTGGTTCGGACGCAGAAGCTTCTGTGATGCTGAAACGCGCTGATGGC TCCGAACTGAGCCATCGTGAGTTCATC (SEQ ID NO: 15) | 75 |
| TpN47_16r | GTAGCTGGCGTCATCACCATAGTAATCATAGCGGACCGTGTTGAAGTT CATCACATAGTCGATGAACTCACGATG (SEQ ID NO: 16) | 75 |
| TpN47_17f | GATGACGCCAGCTACACCAATCTGATGGCGAGTTATGGCACCAAACAC TCGGCTGATTCCTGGTGGAAGCAGGT (SEQ ID NO: 17) | 75 |
| TpN47_18r | ACCTGAGCCTTTAAAGCGATCGAACCCATAGTTGATACCGCACGAAAT GCGCGGCACACGACCTGTCTTCCACCA (SEQ ID NO: 18) | 75 |
| TpN47_19f | TTTAAAGGCTCAGGTCCGGGTTATTACCGTCTGACTTTG (SEQ ID NO: 19) | 39 |
| TpN47_20r | CCCTTCGTATTTCGGCAGGAAGCGCACATCAGCAACTACGTCACGATA GCCGTTGGCAATCAAAGTCAGACGGTA (SEQ ID NO: 20) | 75 |
| TpN47_21f | CCGAAATACGAAGGGAACATCGATATTGGCTTGAAGGGCAAAGTGCTG ACCATCGGGGGTGCGGACGCCGAAACC (SEQ ID NO: 21) | 75 |
| TpN47_22r | TTGATCGCTGACAAGTTTAGGTTGGCCATCGGCAAACACGTCAACTGC AGCATCCATCAGGGTTTCGGCGTCCGC (SEQ ID NO: 22) | 75 |
| TpN47_23f | CTTGTCAGCGATCAAGCGGTGAGCCTGGGGCAGAATGTCCTCTCTGCG GATTTCACTCCGGGCACCGAATACACG (SEQ ID NO: 23) | 75 |
| TpN47_24r | CTCGAGCTACTGGGCCACTACTTTCGCACGCACAGAACCGAACTCTTT GAAGCGCACTTCAACCGTGTATTCGGT (SEQ ID NO: 24) | 75 |

(Artificial Preparation of TpN47 Gene)

A TpN47 gene was synthesized through recursive PCR with reference to nucleotide sequences of a database (GenBank AE000520). Specifically, a DNA fragment encoding the full-length of the TpN47 gene was produced by using a DNA fragment produced through PCR by using a primer pair of TpN47__1f and TpN47__2r having mutually complementary sequences at their ends and a series of the following primer pairs having complementary end sequences: TpN47__3f and TpN47__4r, TpN47__5f and TpN47__6r, TpN47__7f and TpN47__8r, TpN47__9f and TpN47__10r, TpN47__11f and TpN47__12r, TpN47__13f and TpN47__14r, TpN47__15f and TpN47__16r, TpN47__17f and TpN47__18r, TpN47__19f and TpN47__20r, TpN47__21f and TpN47__22r, and TpN47__23f and TpN47__24r. FIG. 1 shows the feature of recursive PCR.

(Construction of TpN47 Antigen Expression Vector)

The thus-prepared TpN47 gene was ligated to the SmaI site of pBluscript II SK(+) (product of Stratagene), and E. coli DH5α (product of Takara Bio) was transformed with the ligation product through the calcium method. Transformation through the calcium method was carried out in the following manner. Specifically, 0.1 mL of an overnight culture solution of E. coli DH5α was inoculated to 5 mL of an LB medium (see Table 2), and shake-culturing was performed at 37° C. until the turbidity reached 0.5. An aliquot (1 mL) of cells was recovered through centrifugation and suspended in 0.5 mL of ice-cooled 50 mM $CaCl_2$. The suspension was allowed to stand on ice for 30 minutes. An aliquot (0.2 mL) of the suspension was sampled, and a plasmid DNA after ligation was added to the suspension. The mixture was allowed to stand on ice for 30 minutes and subjected to heat shock at 42° C. for 30 seconds. 0.8 mL of an SOB medium (see Table 2) was added thereto (total volume: 1 mL). Culturing was performed at 37° C. for one hour, and the culture product was applied to an LB agar medium (see Table 2) containing isopropyl-β-galactopyranoside (hereinafter referred to as IPTG, product of Nacalai Tesque), 5-chloro-4-bromo-3-D-galactose (hereinafter referred to as X-gal, product of Nacalai Tesque), and 100 μg/mL of ampicillin (product of Wako Pure Chemical Industries, Ltd.), followed by culturing overnight at 37° C. Single colonies were selected through blue/white selection. The thus-selected colonies were inoculated to 2 mL of a TB medium (see Table 2) having an ampicillin final concentration of 100 μg/mL, and culturing was performed overnight. From the thus-cultured E. coli cells, plasmid DNA fragments were extracted by means of Favor Prep Plasmid DNA Extraction Mini Kit (product of FAVORGEN BIOTECH CORP.). The thus-extracted plasmids were treated with restriction enzymes and sequenced, to thereby confirm nucleotide sequence.

A plasmid having an appropriate nucleotide sequence of the TpN47 gene was incorporated into the BamHI site and XhoI site of pΔGST, which is produced by removing a GST gene from a commercial vector, pGEX-4T-3 (product of GE Healthcare Bioscience) through 1-day mutagenesis, to thereby construct pΔGST-TpN47. Into the BamHI site of pΔGST-TpN47, 4AaCter (696-851) (SEQ ID NO: 42, hereinafter referred to as Tag)—a part of the amino acid sequence of a Cry protein derived from Bacillus thuringiensis disclosed in WO 2010/013789—was incorporated, to thereby construct pΔGST-Tag-TpN47. Specifically, a gene encoding Tag was produced through recursive PCR. The gene encoding Tag was produced such that the BamHI site was added to the 5' end, and a nucleotide sequence encoding the linker sequence and the BamHI site were added to the 3' end. The gene encoding Tag was inserted to the SmaI site of pBluscript II SK(+) and subjected to cloning and sequencing, whereby the gene was confirmed to have an appropriate nucleotide sequence. Subsequently, the gene encoding Tag was cut from pBluscript II SK(+) by use of BamHI and inserted to the BamHI site of pΔGST-TpN47, to thereby construct pΔGST-Tag-TpN47. FIG. 2 shows the feature of construction of the expression vector. The thus-constructed pΔGST-Tag-TpN47 was incorporated into *E. coli* BL21 (product of Takara Bio) for transformation. The same transformation procedure as described above was employed.

TABLE 2

| | | |
|---|---|---|
| *1) Composition of LB medium (1 L) | | |
| Trypton (Nacalai Tesque) | 10 | g |
| Dry yeast extract (Nacalai Tesque) | 5 | g |
| Sodium chloride (Kishida Chemical) | 1 | g |
| | up to 1,000 | mL |
| Autoclave treatment after preparation | | |
| *2) Composition of LB agar medium (1 L) | | |
| Trypton (Nacalai Tesque) | 10 | g |
| Dry yeast extract (Nacalai Tesque) | 5 | g |
| Sodium chloride (Kishida Chemical) | 10 | g |
| Agar powder (Wako Pure Chemical) | 15 | g |
| | up to 1,000 | mL |
| Autoclave treatment after preparation | | |
| *3) Composition of SOB medium (1 L) | | |
| Trypton (Nacalai Tesque) | 20 | g |
| Dry yeast extract (Nacalai Tesque) | 5 | g |
| Sodium chloride (Kishida Chemical) | 0.5 | g |
| Potassium chloride (Kishida Chemical) | 0.186 | g |
| | up to 1,000 | mL |
| Autoclave treatment after preparation. | | |
| 2M $MgCl_2$ (Kishida chemical) (5 mL) added to the solution at room temp. | | |
| *4) Composition of TB medium (1 L) | | |
| Liquid A | | |
| Trypton (Nacalai Tesque) | 12 | g |
| Dry yeast extract (Nacalai Tesque) | 24 | g |
| Glycerol (Kishida Chemical) | 4 | mL |
| | up to 900 | mL |
| Liquid B | | |
| Dihydrogen potassium phosphate | 2.3 | g |
| Hydrogen dipotassium phosphate | 12.5 | g |
| | up to 100 | mL |

Liquid A, B autoclaved, cooled, and mixed.

(TpN47 Expression)

*E. coli* BL21 to which the pΔGST-Tag-TpN47 expression vector had been incorporated was preliminarily cultured overnight in a TB medium (5 mL) having a final ampicillin concentration of 100 μg/mL. The overnight culture liquid (0.5 mL) was added to an LB medium (50 mL) having a final ampicillin concentration of 100 μg/mL. Culturing was performed by means of a shaker (product of SANYO, model: MIR-S100) at 240 rpm and 37° C. until the OD600 reached 0.6 to 0.8. IPTG was added to the culture to a final concentration of 0.5 mM. Subsequently, further culturing was performed for 3 hours (240 rpm, 37° C.), to thereby induce expression.

(Purification of TpN47)

Expression-induced cells were recovered and suspended in 10 mL of 10 mM phosphate-buffered saline (10 mM phosphate buffer (pH: 7.4), NaCl 0.9 wt. %). The suspended cells were broken through ultrasonication and centrifuged at 9,000 rpm for 10 minutes, to thereby remove an insoluble fraction. The insoluble fraction containing a target protein was centrifugally washed with an appropriate amount of ultrapure water. The thus-precipitated matter was solubilized with a urea solution (8M Urea, 20 mM Tris-HCl, pH: 8.0). The product was used as a solution of a target protein (concentration: 4 mM).

(Primers for Preparation of Genes of Polypeptides 1 to 8)

Table 3 shows the primers for preparing genes corresponding to polypeptides 1 to 8 represented by SEQ ID NOs: 34 to 41 (synthesized by DNA synthesizer).

TABLE 3

Primers for producing TpN47-deleted mutants

| Name | sequence (5'→3') | length |
|---|---|---|
| PP-Bam_3' | GGATCCCGGACCCTGGAAC (SEQ ID NO: 25) | 19 |
| r47_2F | GGTAATGCCGAAGCCGATCGC (SEQ ID NO: 26) | 21 |
| r47_3R | CTTCATACCGTGAACTTTTAC (SEQ ID NO: 27) | 21 |
| r47_3.5F | TTTGTCCCAGTTGCGGTTCC (SEQ ID NO: 28) | 20 |
| r47_4R | TTCCATCGAGCTTACTTTACG (SEQ ID NO: 29) | 21 |
| r47_5F | AGCCCGCACGACCTTGT (SEQ ID NO: 30) | 17 |
| r47_6R | GTATTTCGGCAGGAAGCGCAC (SEQ ID NO: 31) | 21 |
| r47_7F | GAAGGGAACATCGATATTGG (SEQ ID NO: 32) | 20 |
| pGEX_TAA-Xho 5' | TAACTCGAGCGGCCGCATC (SEQ ID NO: 33) | 19 |

(Artificial Preparation of Genes of Polypeptides 1 to 8)

Genes of polypeptides 1 to 8 were prepared through 1-day mutagenesis by use of pΔGST-Tag-TpN47 serving as a template. Specifically, primers were designed so that a segment which was to be deleted from pΔGST-Tag-TpN47 was sandwiched by the primers. By use of the primers, DNA fragments were amplified through PCR in the outward direction of each vector, to thereby produce a DNA fragment encoding each of the polypeptides. Table 4 shows primary pairs for producing the polypeptides. The nucleotide sequences of the polypeptides 1 to 8 are represented by SEQ ID NOs: 34 to 41.

TABLE 4

| | Domain | Templates | | Primer pair |
|---|---|---|---|---|
| Polypeptide 1 | CD | pΔGST-Tag-TpN47 | PP-Bam_3' | r47_5F |
| Polypeptide 2 | A2CD | pΔGST-Tag-TpN47 | PP-Bam_3' | r47_3.5F |
| Polypeptide 3 | BA2CD | pΔGST-Tag-TpN47 | PP-Bam_3' | r47_2F |
| Polypeptide 4 | A1BA2C | pΔGST-Tag-TpN47 | r47_6R | pGEX_TAA_Xho5' |
| Polypeptide 5 | A1BA2 | pΔGST-Tag-TpN47 | r47_4R | r47_5F |
| Polypeptide 6 | B | Polypeptide 3-producing vector | r47_3R | pGEX_TAA_Xho5' |
| Polypeptide 7 | C | Polypeptide 4-producing vector | PP-Bam_3' | r47_5F |
| Polypeptide 8 | D | pΔGST-Tag-TpN47 | PP-Bam_3' | r47_7F |

(Construction of Vectors for Production of Polypeptides 1 to 8)

The aforementioned PCR product was self-ligated with T4 DNA Ligase (product of Takara Bio) and 10× Ligation buffer (product of Takara Bio). Then, a restriction enzyme DpnI (product of Toyobo) was added to the ligation solution, and the mixture was incubated at 37° C. for one hour. The procedure after insertion into *E. coli* was the same as employed in construction of the TpN47 vector.

(Production of Polypeptides 1 to 8)

The procedure of TpN47 expression was repeated, except that an expression vector corresponding to each polypeptide was used.

(Purification of Polypeptides 1 to 8)

The procedure of TpN47 purification was repeated, except that cells of a bacterium inducing production of polypeptides 1 to 8 were used.

(Production of Latex Particles)

To a glass reactor (capacity: 2 L) equipped with a stirrer, a reflux condenser, a temperature sensor, a nitrogen conduit, and a jacket, distilled water (1,100 g), styrene (200 g), sodium styrenesulfonate (0.2 g), and a solution of potassium perfsulfate (1.5 g) in distilled water (50 g) were added. The atmosphere of the reactor was substituted by nitrogen. The mixture was allowed to polymerization at 70° C. for 48 hours under stirring.

After completion of polymerization, the reaction mixture was filtered through filter paper, to thereby recover latex particles. The mean particle size of the thus-yielded latex particles was determined by taking an image of the latex particles under a transmission electron microscope (product of JEOL Ltd., model "JEM-1010") at a magnification of 10,000 and analyzing the image including 100 or more particles. The thus-obtained mean particle size was 0.4 µm.

(Preparation of Anti-*Treponema pallidum* Antibody Assay Reagent)

Example 1

Polypeptide 1 (4 mM) was dissolved in 20 mM Tris buffer (hereinafter referred to as Tris-HCl, pH: 8.0), and 100 µL (0.4 µmol) of the solution was added to 100 µL of a latex solution (solid content: 10% (w/v), mean particle size: 0.4 µm), followed by stirring at 4° C. for one hour. Subsequently, 1 mL of Tris-HCl buffered saline (20 mM Tris-HCl, salt concentration: 0.9 wt. %, pH: 8.0) containing 1% (W/V) bovine serum albumin (hereinafter referred to as BSA, Fraction V, Reagent Grade, product of Miles Corp.) was added thereto, and the resultant mixture was stirred for one hour. The thus-obtained liquid was centrifuged at 10° C. and 15,000 rpm for 15 minutes. To the precipitated solid, 20 mL of 100 mM phosphate buffer (pH: 7.5) containing 1 (w/v) % BSA was added, to thereby suspend the latex, whereby an anti-*Treponema pallidum* antibody assay reagent was prepared.

Example 2

The procedure of Example 1 was repeated, except that polypeptide 2 solution was used as an antigen solution, to thereby prepare an anti-*Treponema pallidum* antibody assay reagent.

Example 3

The procedure of Example 1 was repeated, except that polypeptide 3 solution was used as an antigen solution, to thereby prepare an anti-*Treponema pallidum* antibody assay reagent.

Comparative Example 1

The procedure of Example 1 was repeated, except that purified TpN47 solution was used as an antigen solution, to thereby prepare an anti-*Treponema pallidum* antibody assay reagent.

Comparative Example 2

The procedure of Example 1 was repeated, except that polypeptide 4 solution was used as an antigen solution, to thereby prepare an anti-*Treponema pallidum* antibody assay reagent.

Comparative Example 3

The procedure of Example 1 was repeated, except that polypeptide 5 solution was used as an antigen solution, to thereby prepare an anti-*Treponema pallidum* antibody assay reagent.

Comparative Example 4

The procedure of Example 1 was repeated, except that polypeptide 6 solution was used as an antigen solution, to thereby prepare an anti-*Treponema pallidum* antibody assay reagent.

Comparative Example 5

The procedure of Example 1 was repeated, except that polypeptide 7 solution was used as an antigen solution, to thereby prepare an anti-*Treponema pallidum* antibody assay reagent.

Comparative Example 6

The procedure of Example 1 was repeated, except that polypeptide 8 solution was used as an antigen solution, to thereby prepare an anti-*Treponema pallidum* antibody assay reagent.

(Measurement)

By use of each of the anti-*Treponema pallidum* antibody assay reagents prepared in Examples 1 to 3 and Comparative Examples 1 to 6, anti-*Treponema pallidum* antibody assay was performed in the following manner.

(1) Assay of Anti-*Treponema pallidum* Antibody Standard Solution

An anti-*Treponema pallidum* antibody standard solution was prepared by admixing 15 μL of syphilis-positive standard serum (product of Sekisui Medical Co., Ltd., 5 T.U. (titer unit)*) with 100 μL of a sample diluent (100 mM phosphate buffer (pH: 7.4) containing 1% BSA to which 0.8 (w/v) % Lipidure (Lipidure-BL, product of NOF Corporation) had been added), and maintaining the mixture at 37° C. for an appropriate time. To the thus-obtained mixture, 100 μL of an anti-*Treponema pallidum* antibody assay reagent was added, and the mixture was stirred. The absorbance was monitored at 700 nm from the point in time of about 80 seconds to that of 300 seconds, to thereby obtain change in absorbance (ΔAbs). The measurement was performed by means of an auto-analyzer 7170.

Figure 3:
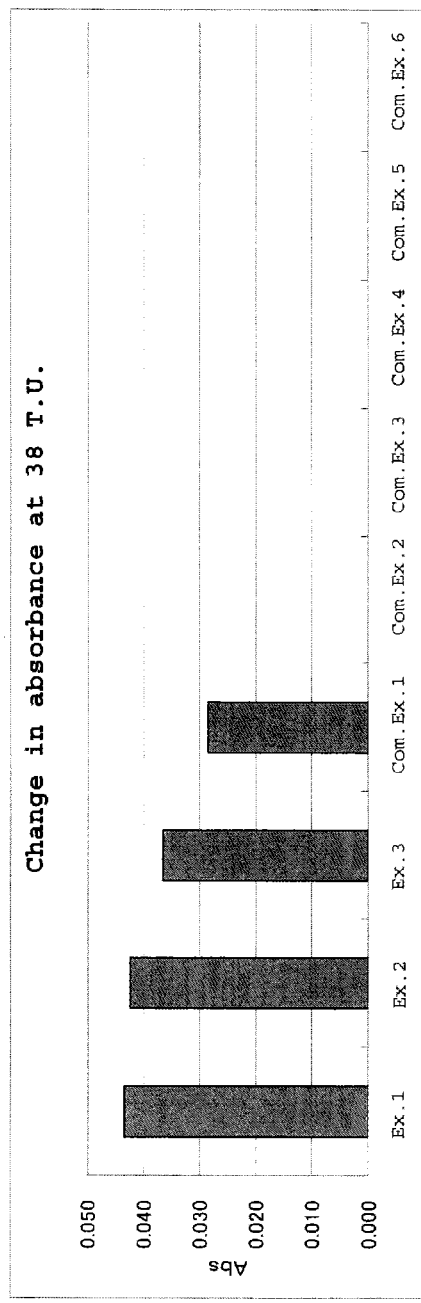
FIG. 3 A graph showing changes in absorbance at 38 T.U. provided by antigens.
Figure 4:
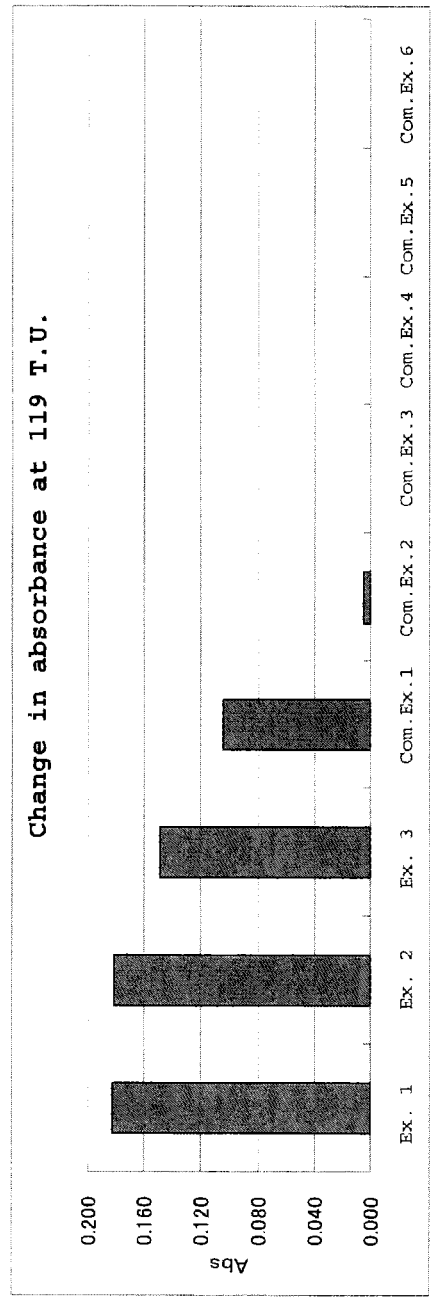
FIG. 4 A graph showing changes in absorbance at 119 T.U. provided by antigens.
Figure 5:
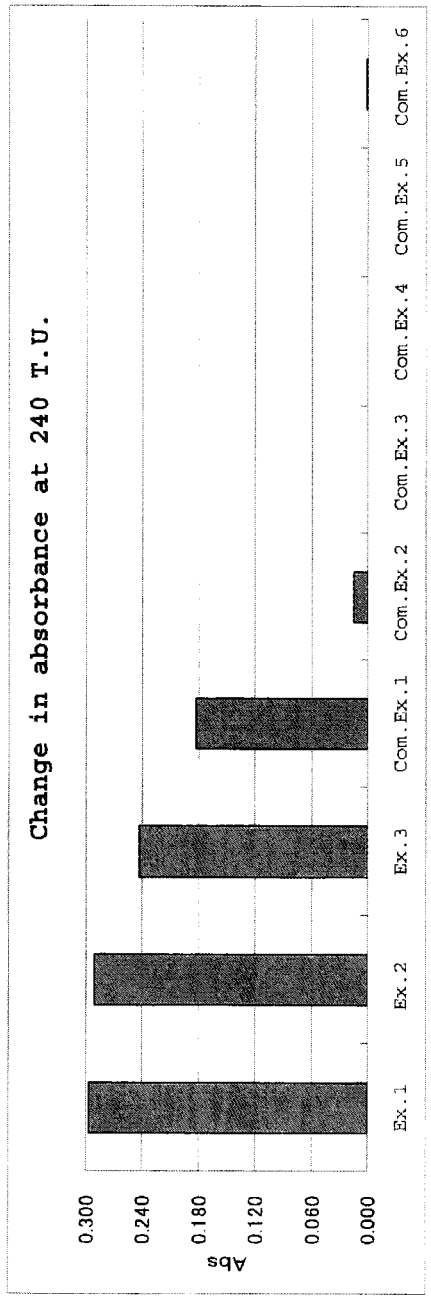
FIG. 5 A graph showing changes in absorbance at 240 T.U. provided by antigens.

Table 5 and FIGS. 3 to 5 show the results. As is clear from Table 5 and FIGS. 3 to 5, the assay reagents prepared in the Example were found to exhibit high reactivity.

As used herein, the unit *T.U. refers to a titer unit, which is a unit of the anti-*Treponema pallidum* antibody titer determined by use of Mediace (Registered trademark) TPLA, product of Sekisui Medical Co., Ltd.). When the international standard sample is assayed, 1 T.U. is equivalent to 2 mIU.

TABLE 5

Sensitivity of domains

| | Domain | | 38 T.U. | 119 T.U. | 240 T.U. |
|---|---|---|---|---|---|
| Polypeptide 1 | CD | Ex. 1 | 0.0435 | 0.1828 | 0.2972 |
| Polypeptide 2 | A2CD | Ex. 2 | 0.0424 | 0.1826 | 0.2918 |
| Polypeptide 3 | BA2CD | Ex. 3 | 0.0365 | 0.1490 | 0.2429 |
| TpN47 | A1BA2CD | Comp. Ex. 1 | 0.0286 | 0.1044 | 0.1823 |
| Polypeptide 4 | A1BA2C | Comp. Ex. 2 | 0.0000 | 0.0046 | 0.0153 |
| Polypeptide 5 | A1BA2 | Comp. Ex. 3 | 0.0000 | 0.0000 | 0.0002 |
| Polypeptide 6 | B | Comp. Ex. 4 | 0.0000 | 0.0000 | 0.0000 |
| Polypeptide 7 | C | Comp. Ex. 5 | 0.0000 | 0.0000 | 0.0000 |
| Polypeptide 8 | D | Comp. Ex. 6 | 0.0000 | 0.0000 | 0.0013 |

ΔAbs (2) Assay of Positive Sample

The procedure of (1) above was repeated, except that serum samples which had been evaluated as syphilis-positive (≥10 T.U) were assayed, to thereby obtain change in absorbance (ΔAbs). By use of a calibration curve drawn from the results of standard sample assay (1), antibody titer was calculated. The correlation of the antibody titer of each of the anti-*Treponema pallidum* antibody assay reagents prepared in the Examples and the Comparative Examples and that of a commercial reagent Mediace (Registered trademark) TPLA, product of Sekisui Medical Co., Ltd.) was investigated. Table 6 shows the results (x: commercial reagent, y: each of the anti-*Treponema pallidum* antibody assay reagents prepared in Examples 1 to 3 and Comparative Example 1). As is clear from Table 6, the reagents prepared in the Examples have high correlation with a commercial assay reagent in terms of antibody titer.

TABLE 6

Correlation test

| | Ex. 1 | Ex. 2 | Ex. 3 | Comp. Ex. 1 |
|---|---|---|---|---|
| Peptide Domain | Polypeptide 1 CD | Polypeptide 2 A2CD | Polypeptide 3 BA2CD | TpN47 A1BA2CD |
| Regression equation | y = 0.95x + 2.71 | y = 0.90x + 1.85 | y = 0.92x + 14.0 | y = 0.93x + 24.8 |
| Correlation coeff. | 0.965 | 0.958 | 0.886 | 0.798 | x: Mediace TPLA,
y: Reagent (Ex. or Comp. Ex.)

(3) Assay of Negative Samples

The procedure of (1) above was repeated, except that serum samples which had been evaluated as syphilis-negative (0 T.U) were assayed, to thereby obtain change in absorbance (ΔAbs). By use of a calibration curve drawn from the results of standard sample assay (1), antibody titer was calculated.

Table 7 shows the results. In the immunoassay, the sample is evaluated as syphilis-positive when the titer unit is 10 T.U. or higher. In Comparative Example 1, various non-specific reactions occurred, and many false positive samples were observed. In contrast, in Examples 1 to 3, no substantial non-specific reaction occurred, and no false positive case was observed.

TABLE 7

Neg. Sample analysis

| | Ex. 1 | Ex. 2 | Ex. 3 | Comp. Ex. 1 |
|---|---|---|---|---|
| Domain | CD | A2CD | BA2CD | A1BA2CD |
| Neg. 1 | 0 | 0 | 0 | 20 |
| Neg. 2 | 0 | 6 | 9 | 26 |
| Neg. 3 | 0 | 0 | 0 | 7 |
| Neg. 4 | 0 | 0 | 2 | 4 |
| Neg. 5 | 0 | 0 | 0 | 9 |
| Neg. 6 | 0 | 0 | 1 | 5 |

T.U.

INDUSTRIAL APPLICABILITY

Use of the recombinant antigen of the present invention enables provision of an anti-*Treponema pallidum* antibody assay reagent which realizes high-sensitivity, high-specificity assay of an anti-*Treponema pallidum* antibody.

The invention claimed is:

1. A reagent for assaying anti-*Treponema pallidum* antibody, based on an antigen-antibody reaction, wherein the reagent comprises, as an antigen, a recombinant polypeptide comprising at least domain C and domain D of *Treponema pallidum* 47 kDa antigen encoded by the nucleic acid comprising SEQ ID NO:34 and lacking domain A1 of the 47 kDa antigen, wherein the domain A1 is formed of amino acids 1-34 of domain A of the *Treponema pallidum* 47 kDa antigen, wherein the positions of amino acids are counted form the N-terminus of the 47 kDa antigen.

2. The anti-*Treponema pallidum* antibody assay reagent according to claim 1, wherein the antigen is a recombinant polypeptide formed of domain C and domain D; domain A2, domain C, and domain D; or domain B, domain A2, domain C, and domain D, of *Treponema pallidum* 47 kDa antigen.

3. The anti-*Treponema pallidum* antibody assay reagent according to claim 1, wherein the antigen is supported on an insoluble carrier.

4. The anti-*Treponema pallidum* antibody assay reagent according to claim 2, wherein the antigen is supported on an insoluble carrier.

5. The anti-*Treponema pallidum* antibody assay reagent according to claim 3, wherein the insoluble carrier is a polymer latex.

6. The anti-*Treponema pallidum* antibody assay reagent according to claim 4, wherein the insoluble carrier is a polymer latex.

7. The anti-*Treponema pallidum* antibody assay reagent according to claim 1, wherein the recombinant polypeptide consists of domain C and domain D of *Treponema pallidum* 47 kDa antigen.

8. A reagent for assaying anti-*Treponema pallidum* antibody based on an antigen-antibody reaction, wherein the reagent comprises, as an antigen, a recombinant polypeptide comprising at least domain A2, domain C, and domain D of *Treponema pallidum* 47 kDa antigen encoded by the nucleic acid comprising SEQ ID NO:35 and lacking domain A1 of the 47 kDa antigen, wherein the domain A1 is formed of amino acids 1-34 of domain A of the *Treponema pallidum* 47 kDa antigen, wherein the positions of amino acids are counted form the N-terminus of the 47 kDa antigen.

9. The method for assaying anti-*Treponema pallidum* antibody, characterized in that the method employs an anti-*Treponema pallidum* antibody assay reagent as recited in claim 1.

10. A method for assaying anti-*Treponema pallidum* antibody, characterized in that the method employs an anti-*Treponema pallidum* antibody assay reagent as recited in claim 2.

11. A method for assaying anti-*Treponema pallidum* antibody, characterized in that the method employs an anti-*Treponema pallidum* antibody assay reagent as recited in claim 3.

12. A method for assaying anti-*Treponema pallidum* antibody, characterized in that the method employs an anti-*Treponema pallidum* antibody assay reagent as recited in claim 4.

13. A method for assaying anti-*Treponema pallidum* antibody, characterized in that the method employs an anti-*Treponema pallidum* antibody assay reagent as recited in claim 5.

14. A method for assaying anti-*Treponema pallidum* antibody, characterized in that the method employs an anti-*Treponema pallidum* antibody assay reagent as recited in claim 6.

* * * * *